United States Patent
Barnes (10) Patent No.: US 12,343,032 B2
(45) Date of Patent: Jul. 1, 2025

(54) SURGICAL CUTTING DEVICE FOR ULTRASONIC GUIDED SOFT TISSUE SURGERY

(71) Applicant: Sonex Health, Inc., Eagan, MN (US)

(72) Inventor: Darryl E. Barnes, Eagan, MN (US)

(73) Assignee: Sonex Health, Inc., Eagan, MN (US)

( * ) Notice: Subject to any disclaimer, the term of this patent is extended or adjusted under 35 U.S.C. 154(b) by 0 days.

(21) Appl. No.: 18/652,282

(22) Filed: May 1, 2024

(65) Prior Publication Data
US 2024/0293142 A1     Sep. 5, 2024

Related U.S. Application Data

(63) Continuation of application No. 17/647,391, filed on Jan. 7, 2022, now Pat. No. 12,004,767.
(Continued)

(51) Int. Cl.
*A61B 17/32* (2006.01)
*A61B 17/00* (2006.01)

(52) U.S. Cl.
CPC ......... *A61B 17/320036* (2013.01); *A61B 2017/00367* (2013.01); *A61B 2017/0042* (2013.01);
(Continued)

(58) Field of Classification Search
CPC ....... A61M 5/178; A61B 2017/320028; A61B 2017/320012; A61B 2017/22071;
(Continued)

(56) References Cited

U.S. PATENT DOCUMENTS 2,123,768 A    7/1938  Corsico-Piccolini et al.
3,435,826 A    4/1969  Fogarty
(Continued)

FOREIGN PATENT DOCUMENTS

DE    4444166 A1    6/1996
EP    0818208 B1    7/2002
(Continued)

OTHER PUBLICATIONS

Extended European Search Report for European Application No. 227373479, dated Oct. 24, 2024. (11 Pages).
(Continued)

*Primary Examiner* — Shaun L David
*Assistant Examiner* — Mitchell Brian Hoag
(74) *Attorney, Agent, or Firm* — Seager, Tufte & Wickhem LLP (57) ABSTRACT

The presently disclosed subject matter relates generally to a device for cutting soft tissue, such as transverse carpal ligaments and annular ligaments of the finger, and methods of using the soft tissue cutting device. A soft tissue cutting device includes an inner tubular member extending between a distal end and a proximal end of the inner tube, an outer tubular member disposed over at least a portion of the inner tubular member and movable between an initial position and an extended position, an outer tubular member movement controller that controls movement of the outer tubular member between the initial position and the extended position, and an attachment mechanism for removably coupling the proximal end of the inner tubular member to a dispensing member. A distal end of the outer tubular member includes a cutting member.

22 Claims, 5 Drawing Sheets

Related U.S. Application Data (60) Provisional application No. 63/135,352, filed on Jan. 8, 2021.

(52) U.S. Cl.
CPC ..... *A61B 2017/00738* (2013.01); *A61B 17/32* (2013.01); *A61B 2017/320012* (2013.01); *A61B 2017/320028* (2013.01); *A61B 2017/320048* (2013.01); *A61B 2017/32007* (2017.08); *A61B 2017/320075* (2017.08)

(58) Field of Classification Search
CPC ........... A61B 2017/00893; A61B 2017/00738; A61B 2017/0042; A61B 2017/00367; A61B 17/32; A61B 2017/320075; A61B 2017/32007; A61B 17/320036; A61B 17/3211; A61B 17/320016; A61B 17/32002; A61B 18/148; A61B 2017/320008; A61B 18/1477; A61B 17/32093; A61B 17/3209; A61B 2017/320048
See application file for complete search history.

(56) References Cited

U.S. PATENT DOCUMENTS

| | | | |
|---|---|---|---|
| 4,962,770 A | 10/1990 | Agee et al. | |
| 4,963,147 A | 10/1990 | Agee et al. | |
| 4,979,951 A | 12/1990 | Simpson | |
| 5,089,000 A | 2/1992 | Agee et al. | |
| 5,125,927 A | 6/1992 | Belanger | |
| 5,217,007 A * | 6/1993 | Ciaglia | A61M 16/0472 |
| | | | 128/207.29 |
| 5,306,284 A | 4/1994 | Agee et al. | |
| 5,325,883 A | 7/1994 | Orr | |
| 5,345,927 A | 9/1994 | Bonutti | |
| 5,425,355 A | 6/1995 | Kulick | |
| 5,569,283 A | 10/1996 | Green et al. | |
| 5,620,446 A | 4/1997 | McNamara et al. | |
| 5,649,946 A | 7/1997 | Bramlet | |
| 5,655,545 A | 8/1997 | Johnson et al. | |
| 5,690,663 A | 11/1997 | Stephens | |
| 5,690,664 A | 11/1997 | Sauer et al. | |
| 5,702,417 A | 12/1997 | Hermann | |
| 5,707,382 A | 1/1998 | Sierocuk et al. | |
| 5,709,697 A | 1/1998 | Ratcliff et al. | |
| 5,735,865 A | 4/1998 | Schaumann et al. | |
| 5,755,732 A | 5/1998 | Green et al. | |
| 5,766,198 A | 6/1998 | Li | |
| 5,769,865 A | 6/1998 | Kermode et al. | |
| 5,769,895 A | 6/1998 | Ripamonti | |
| 5,772,680 A | 6/1998 | Kieturakis et al. | |
| 5,779,053 A | 7/1998 | Partika et al. | |
| 5,782,854 A | 7/1998 | Hermann | |
| 5,800,449 A | 9/1998 | Wales | |
| 5,810,806 A | 9/1998 | Ritchart et al. | |
| 5,813,977 A | 9/1998 | Hinchliffe et al. | |
| 5,827,311 A | 10/1998 | Berelsman et al. | |
| 5,860,997 A | 1/1999 | Bonutti | |
| 5,865,728 A | 2/1999 | Moll et al. | |
| 5,893,861 A | 4/1999 | Yumoto | |
| 5,904,699 A | 5/1999 | Schwemberger et al. | |
| 5,908,433 A | 6/1999 | Eager et al. | |
| 5,954,739 A | 9/1999 | Bonutti | |
| 5,957,944 A | 9/1999 | Khuri et al. | |
| 5,964,740 A * | 10/1999 | Ouchi | A61M 25/0068 |
| | | | 604/164.01 |
| 5,968,061 A | 10/1999 | Mirza | |
| 6,004,337 A | 12/1999 | Kieturakis et al. | |
| 6,007,554 A | 12/1999 | Van Ess | |
| 6,012,586 A | 1/2000 | Misra | |
| 6,015,421 A | 1/2000 | Echeverry et al. | |
| 6,017,356 A | 1/2000 | Frederick et al. | |
| 6,019,774 A * | 2/2000 | Weiss | A61B 17/320036 |
| | | | 606/167 |
| 6,030,402 A | 2/2000 | Thompson et al. | |
| 6,080,175 A | 6/2000 | Hogendijk | |
| 6,083,177 A | 7/2000 | Kobren et al. | |
| 6,106,496 A | 8/2000 | Arnissolle | |
| 6,113,617 A | 9/2000 | Van Der Merwe | |
| 6,117,153 A | 9/2000 | Lary et al. | |
| 6,168,608 B1 | 1/2001 | Echeverry et al. | |
| 6,171,236 B1 | 1/2001 | Bonutti | |
| 6,179,852 B1 | 1/2001 | Strickland et al. | |
| 6,217,602 B1 | 4/2001 | Redmon | |
| 6,258,113 B1 | 7/2001 | Adams et al. | |
| 6,264,604 B1 | 7/2001 | Kieturakis et al. | |
| 6,346,085 B1 | 2/2002 | Schiffman | |
| 6,358,251 B1 | 3/2002 | Mirza | |
| 6,361,543 B1 | 3/2002 | Chin et al. | |
| 6,402,770 B1 | 6/2002 | Jessen | |
| 6,447,529 B2 | 9/2002 | Fogarty et al. | |
| 6,451,042 B1 | 9/2002 | Bonutti | |
| 6,514,272 B1 | 2/2003 | Kieturakis et al. | |
| 6,565,590 B2 | 5/2003 | Kieturakis et al. | |
| 6,592,602 B1 | 7/2003 | Peartree et al. | |
| 6,632,234 B2 | 10/2003 | Kieturakis et al. | |
| 6,685,717 B1 | 2/2004 | Ilic | |
| 6,746,465 B2 | 6/2004 | Diederich et al. | |
| 6,875,183 B2 | 4/2005 | Cervi | |
| 6,896,141 B2 | 5/2005 | McMichael et al. | |
| 7,001,405 B2 | 2/2006 | Kieturakis et al. | |
| 7,037,317 B2 | 5/2006 | Hermann et al. | |
| 7,214,236 B2 | 5/2007 | Kieturakis et al. | |
| 7,329,253 B2 | 2/2008 | Brounstein et al. | |
| 7,331,462 B2 | 2/2008 | Steppe | |
| 7,434,687 B2 | 10/2008 | Itou et al. | |
| 7,476,235 B2 | 1/2009 | Diederich et al. | |
| 7,481,817 B2 | 1/2009 | Sauer | |
| 7,504,875 B2 | 3/2009 | Bhushan et al. | |
| 7,520,886 B2 | 4/2009 | Surti | |
| 7,628,798 B1 | 12/2009 | Welborn | |
| 7,708,751 B2 | 5/2010 | Hughes et al. | |
| 7,744,617 B2 | 6/2010 | Lunsford et al. | |
| 7,780,690 B2 | 8/2010 | Rehnke | |
| 7,918,784 B2 | 4/2011 | Welborn et al. | |
| 7,967,137 B2 | 6/2011 | Fulbrook et al. | |
| 8,052,710 B2 | 11/2011 | Kambin et al. | |
| 8,105,342 B2 | 1/2012 | Onuki et al. | |
| 8,147,487 B2 | 4/2012 | Burbank et al. | |
| 8,177,064 B2 | 5/2012 | McCormick et al. | |
| 8,246,646 B2 | 8/2012 | Kambin et al. | |
| 8,252,013 B2 | 8/2012 | Leibowitz et al. | |
| D666,725 S | 9/2012 | McCormack et al. | |
| 8,257,379 B2 | 9/2012 | Lee | |
| 8,273,098 B2 | 9/2012 | Strickland | |
| 8,282,665 B2 | 10/2012 | Kieturakis et al. | |
| 8,323,278 B2 | 12/2012 | Brecheen et al. | |
| D673,683 S | 1/2013 | McCormack et al. | |
| D674,489 S | 1/2013 | McCormack et al. | |
| 8,348,966 B2 | 1/2013 | McCormack et al. | |
| 8,419,728 B2 | 4/2013 | Klotz et al. | |
| 8,449,478 B2 | 5/2013 | Lee et al. | |
| 8,486,097 B2 * | 7/2013 | Mark | A61B 10/0275 |
| | | | 606/171 |
| 8,500,770 B2 | 8/2013 | Echevery et al. | |
| 8,523,891 B2 | 9/2013 | Welborn | |
| 8,523,892 B2 * | 9/2013 | Rehnke | A61B 1/313 |
| | | | 606/167 |
| 8,603,124 B1 | 12/2013 | Hatch | |
| 8,603,738 B2 | 12/2013 | Condeelis et al. | |
| 8,608,738 B2 | 12/2013 | Brecheen et al. | |
| 8,608,763 B1 | 12/2013 | Jurbala | |
| 8,613,745 B2 | 12/2013 | Bleich | |
| 8,652,157 B2 | 2/2014 | McCormack et al. | |
| 8,672,960 B2 | 3/2014 | Briganti et al. | |
| 8,702,654 B2 | 4/2014 | Agee et al. | |
| 8,721,668 B2 | 5/2014 | McCormack et al. | |
| 8,746,452 B2 | 6/2014 | Tomes et al. | |
| 8,753,364 B2 | 6/2014 | McCormack et al. | |
| 8,876,845 B2 | 11/2014 | Suddaby | |
| 8,906,040 B2 | 12/2014 | Filipi et al. | |

(56) References Cited

U.S. PATENT DOCUMENTS

| | | |
|---|---|---|
| 8,911,470 B2 | 12/2014 | Mirza et al. |
| 8,951,273 B1 | 2/2015 | Fard |
| 8,992,424 B2 | 3/2015 | Orbay et al. |
| 9,017,354 B2 | 4/2015 | Fink et al. |
| 9,028,516 B2 | 5/2015 | Palmer et al. |
| 9,050,004 B2 | 6/2015 | Diao et al. |
| 9,113,953 B2 | 8/2015 | Smith |
| 9,131,951 B2 | 9/2015 | Mirza et al. |
| 9,168,057 B2 | 10/2015 | Poulsen |
| 9,186,217 B2 | 11/2015 | Goyal |
| 9,532,847 B2 | 1/2017 | Hendrickson et al. |
| 10,292,726 B2* | 5/2019 | O'Neil ............ A61B 17/32 |
| 10,874,552 B2* | 12/2020 | Wells ............ A61F 9/00754 |
| 11,259,837 B2 | 3/2022 | Aklog et al. |
| 2002/0120211 A1 | 8/2002 | Wardle et al. |
| 2002/0161387 A1 | 10/2002 | Blanco |
| 2002/0185406 A1 | 12/2002 | Massengale et al. |
| 2004/0143280 A1 | 7/2004 | Suddaby |
| 2004/0195131 A1 | 10/2004 | Spolidoro |
| 2004/0225180 A1 | 11/2004 | Junger |
| 2004/0243023 A1 | 12/2004 | Grigoryants et al. |
| 2004/0267253 A1* | 12/2004 | Klotz ............ A61N 7/02 606/41 |
| 2005/0038423 A1* | 2/2005 | Makin ............ A61N 7/02 607/96 |
| 2005/0209624 A1 | 9/2005 | Vijay |
| 2005/0222598 A1 | 10/2005 | Ho et al. |
| 2005/0228426 A1 | 10/2005 | Campbell |
| 2006/0129128 A1 | 6/2006 | Sampson |
| 2006/0149136 A1 | 7/2006 | Seto et al. |
| 2006/0190021 A1* | 8/2006 | Hausman ............ A61B 17/3496 606/167 |
| 2007/0083225 A1 | 4/2007 | Kiser et al. |
| 2007/0112366 A1 | 5/2007 | Welborn et al. |
| 2007/0118170 A1 | 5/2007 | Kieturakis et al. |
| 2007/0185512 A1* | 8/2007 | Kirchhevel ........ A61F 9/00763 606/170 |
| 2007/0208271 A1 | 9/2007 | Voegele |
| 2007/0225740 A1 | 9/2007 | Suddaby |
| 2008/0033466 A1 | 2/2008 | Assell et al. |
| 2008/0058588 A1 | 3/2008 | Emanuel |
| 2008/0058846 A1 | 3/2008 | Vosough |
| 2008/0109021 A1 | 5/2008 | Medoff |
| 2008/0195128 A1 | 8/2008 | Orbay et al. |
| 2008/0234713 A1 | 9/2008 | Bernardini |
| 2008/0288041 A1 | 11/2008 | Holman et al. |
| 2009/0048620 A1 | 2/2009 | Weiss et al. |
| 2009/0048623 A1 | 2/2009 | Lafosse et al. |
| 2009/0125044 A1 | 5/2009 | Lary |
| 2009/0171157 A1 | 7/2009 | Diederich et al. |
| 2009/0312740 A1 | 12/2009 | Kim et al. |
| 2009/0312807 A1* | 12/2009 | Boudreault ........ A61B 17/3421 606/86 R |
| 2010/0010530 A1 | 1/2010 | Rhee |
| 2010/0100114 A1 | 4/2010 | Berger |
| 2010/0125266 A1 | 5/2010 | Deem et al. |
| 2010/0185222 A1 | 7/2010 | Keller |
| 2010/0211082 A1 | 8/2010 | Sauer |
| 2010/0249719 A1 | 9/2010 | Fojtik |
| 2011/0087258 A1 | 4/2011 | Sluss |
| 2011/0112563 A1 | 5/2011 | To et al. |
| 2011/0118601 A1 | 5/2011 | Barnes et al. |
| 2011/0155599 A1 | 6/2011 | Yakel et al. |
| 2011/0201881 A1 | 8/2011 | Emch |
| 2011/0224710 A1* | 9/2011 | Bleich ............ A61B 17/1671 606/171 |
| 2012/0016398 A1 | 1/2012 | Strickland |
| 2012/0029542 A1* | 2/2012 | Huang ............ A61B 17/320036 606/167 |
| 2012/0029543 A1 | 2/2012 | Lee |
| 2012/0191116 A1 | 7/2012 | Flynn et al. |
| 2012/0198703 A1 | 8/2012 | Ranieri et al. |
| 2012/0203220 A1 | 8/2012 | Brannan et al. |
| 2012/0289987 A1 | 11/2012 | Wilson et al. |
| 2012/0303018 A1 | 11/2012 | Ladtkow et al. |
| 2013/0046323 A1 | 2/2013 | Whitaker |
| 2013/0066149 A1 | 3/2013 | Mirza et al. |
| 2013/0144318 A1 | 6/2013 | Dinis Carmo |
| 2013/0165962 A1 | 6/2013 | Porshinsky et al. |
| 2013/0172895 A1 | 7/2013 | Wallace et al. |
| 2013/0197553 A1 | 8/2013 | Ng et al. |
| 2013/0211201 A1 | 8/2013 | Wongsiri |
| 2013/0289596 A1 | 10/2013 | Guo |
| 2013/0345515 A1 | 12/2013 | Fitzmaurice |
| 2014/0000512 A1 | 1/2014 | Clauss et al. |
| 2014/0012076 A1 | 1/2014 | Mirza et al. |
| 2014/0031621 A1 | 1/2014 | Liu |
| 2014/0039533 A1 | 2/2014 | Palmer et al. |
| 2014/0054356 A1 | 2/2014 | Hartwick et al. |
| 2014/0180282 A1 | 6/2014 | Brecheen et al. |
| 2014/0212456 A1 | 7/2014 | Vazquez-Cintron et al. |
| 2014/0276741 A1 | 9/2014 | McKay |
| 2014/0276790 A1 | 9/2014 | Raybin et al. |
| 2014/0343357 A1* | 11/2014 | Mirza ............ A61B 1/00154 600/104 |
| 2014/0371526 A1 | 12/2014 | Mirza et al. |
| 2015/0018822 A1 | 1/2015 | Racz |
| 2015/0045822 A1 | 2/2015 | Mirza et al. |
| 2015/0073461 A1 | 3/2015 | McCormack et al. |
| 2015/0080878 A1 | 3/2015 | Feng et al. |
| 2015/0080905 A1 | 3/2015 | Begemann et al. |
| 2015/0133982 A1 | 5/2015 | Park |
| 2015/0182248 A1 | 7/2015 | Palmer et al. |
| 2015/0196743 A1 | 7/2015 | Diederich et al. |
| 2015/0201959 A1 | 7/2015 | Guo |
| 2015/0265818 A1 | 9/2015 | Piskun et al. |
| 2015/0282832 A1 | 10/2015 | Mirza et al. |
| 2015/0320436 A1 | 11/2015 | Agee et al. |
| 2016/0071710 A1* | 3/2016 | Hofstadler ............ H01J 49/02 250/282 |
| 2016/0081710 A1 | 3/2016 | Barnes et al. |
| 2016/0157880 A1* | 6/2016 | Aklog ............ A61B 17/3209 606/45 |
| 2016/0175003 A1* | 6/2016 | Kafiluddi ............ A61B 17/3401 604/158 |
| 2016/0235431 A1* | 8/2016 | Brown ............ A61B 17/320016 |
| 2017/0042565 A1 | 2/2017 | Ellsworth et al. |
| 2017/0086803 A1 | 3/2017 | Nakanishi et al. |
| 2017/0105792 A1 | 4/2017 | Barnes et al. |
| 2018/0098758 A1 | 4/2018 | Nishina et al. |
| 2019/0262024 A1 | 8/2019 | Barnes et al. |
| 2019/0366042 A1 | 12/2019 | Garrison et al. |
| 2020/0037855 A1* | 2/2020 | Kim ............ A61B 1/05 |
| 2020/0197087 A1* | 6/2020 | Azam ............ A61B 17/3423 |
| 2021/0212722 A1 | 7/2021 | Kiev et al. |
| 2022/0096117 A1 | 3/2022 | McFarland |

FOREIGN PATENT DOCUMENTS

| | | |
|---|---|---|
| EP | 3193748 A1 | 7/2017 |
| EP | 3278749 A1 | 2/2018 |
| EP | 3766440 A1 | 1/2021 |
| EP | 3908215 A1 | 11/2021 |
| EP | 3975889 A1 | 4/2022 |
| WO | 2007016141 A2 | 2/2007 |
| WO | 2013155472 A1 | 10/2013 |
| WO | 2014118752 A2 | 8/2014 |
| WO | 2014176206 A2 | 10/2014 |
| WO | 2014176206 A3 | 1/2015 |
| WO | 2018231617 A1 | 12/2018 |
| WO | 2020247476 A1 | 12/2020 |
| WO | 2022150837 A1 | 7/2022 |
| WO | 2022232582 A1 | 11/2022 |

OTHER PUBLICATIONS

International Search Report and Written Opinion dated Mar. 25, 2022 for International Application No. PCT/US22/70088.

U.S. Appl. No. 62/086,950, filed Dec. 3, 2014, 52 pages.

International Search Report and Written Opinion mailed Feb. 15, 2016, issued in International Application No. PCT/US2015/049558, 24 pages.

(56) References Cited

OTHER PUBLICATIONS

Examination Report issued in European Patent Application No. 15767038.1, dated Apr. 29, 2019, 8 pages.
International Search Report and Written Opinion issued Sep. 21, 2020, in International Application No. PCT/US20/35094.
Extended European Search Report for Application No. 20738258.1, dated Feb. 23, 2022.
International Search Report and Written Opinion mailed Jun. 15, 2020, in Application No. PCT/US20/12682.

* cited by examiner

SURGICAL CUTTING DEVICE FOR ULTRASONIC GUIDED SOFT TISSUE SURGERY

RELATED APPLICATION

The present application is a continuation application of U.S. application Ser. No. 17/647,391, filed Jan. 7, 2022, which claims priority U.S. Provisional Patent Application No. 63/135,352, filed Jan. 8, 2021, the entire contents of which are incorporated herein by reference.

TECHNICAL FIELD

The present invention generally relates to a soft tissue cutting device and soft tissue cutting methods. The present invention also relates generally to a transverse carpal ligament cutting device, a pulley cutting device, and soft tissue cutting methods.

BACKGROUND

Carpal tunnel syndrome affects approximately 3.7% of the general population and up to 7% of manual labor workers. Several varying surgical procedures are performed annually to treat patients with carpal tunnel syndrome. One of these surgical procedures is known as a carpal tunnel release procedure ("CTR procedure"). During the CTR procedure a transverse carpal ligament is cut in order to reduce median nerve compression and carpal tunnel pressures in the carpal tunnel region.

CTR procedures can be performed by accessing the carpal tunnel primarily from the outside, or accessing the carpal tunnel primarily from the inside. In the former, a palmar incision of various sizes is used to directly visualize and transect the transverse carpal ligament. In the latter, the transverse carpal ligament is visualized from within the carpal tunnel using either an endoscope advanced through a small palmar and/or proximal wrist incision, or ultrasound guidance. These visualization methods are important, as it is hard to visualize individual anatomical variations in the carpal tunnel region, as well as the transverse carpal ligament and at-risk structures nearby (e.g., a median nerve and an ulnar artery). Poor visualization can cause incomplete release of the transverse carpal ligament, or cause injuries to nearby structures.

While ultrasound guidance with CTR procedures enable better visualization of the carpal tunnel region during the procedure, there are still concerns associated with these procedures. One concern is that a sharp cutting instrument may be passed into the carpal tunnel without the ability to precisely control deployment of a sharp cutting instrument. Thus, the sharp cutting instrument presents a risk to both the patient and the operator. It would be desirable to provide an improved device that includes a sharp cutting instrument that is not exposed until the cutting of the transverse carpal ligament is required (i.e., after proper positioning).

Also, because cutting instruments often require the use of two hands, several operators use ultrasound guidance to place a sharp cutting instrument in position to cut the transverse carpal ligament, but then abandon the ultrasound visualization during the actual cutting, as they are unable to simultaneously hold the ultrasound probe, and cut the ligament. It would be desirable to provide an improved device that allows an operator to continue using ultrasound guidance during cutting.

Further, it would be desirable to provide such a device that is capable of administering an anesthetic. Prior to the commencement of the CTR procedure, an anesthetic is injected subcutaneously at the palmar incision site. Additionally, an anesthetic is injected with ultrasound guidance, intracarpally, and may also be injected to areas surrounding the carpal ligament. The anesthetic-containing syringe must be withdrawn from the carpal ligament area to enable the cutting device to be inserted into the wrist, with ultrasound guidance, to perform the CTR procedure. There exists a risk of nerve or artery damage when inserting instruments into the wrist and hand. This risk is increased by the insertion of two independent instruments, namely, the anesthetic-containing syringe, followed by the CTR cutting device. Thus, it would be desirable to provide a device that can perform both functions of delivering the anesthetic, and performing the ligament cutting.

SUMMARY

The present disclosure provides a device for cutting soft tissue that is capable of administering an anesthetic to a cutting site.

A first aspect of the disclosure provides a soft tissue cutting device including an inner tubular member having an internal chamber extending between a distal end and a proximal end of the inner tube, an outer tubular member disposed over at least a portion of the inner tubular member and movable between an initial position and an extended position, a movement controller that controls movement of the outer tubular member between the initial position and the extended position, and an attachment mechanism for removably coupling the proximal end of the inner tubular member to a dispensing member. A distal end of the outer tubular member may include a cutting member.

In some embodiments, the movement controller includes a thumb slide attached to a surface of the outer tubular member. In some embodiments, the outer tubular member movement mechanism further includes a housing disposed around a portion of the outer tubular member distal end; and the thumb slide extends through a portion of a surface of the thumb slide housing. In some embodiments, the handle is molded to allow for single handed use of the soft tissue cutting device. In some embodiments, the thumb slide is lockable.

In some embodiments, the attachment mechanism is a locking mechanism. In some embodiments, the locking mechanism is a luer lock. In some embodiments, the cutting member is a blade having a cutting edge. In some embodiments, the dispensing member is a syringe. In some embodiments, the dispensing member includes a dispensing tube and a depressible member disposed within the dispensing tube, and the depressible member is movable from an initial position to an extended position within the dispensing tube to expel the fluid from the barrel into the inner tubular member. In some embodiments, the dispensing tube is removably attached to a distal end of the attachment mechanism.

In some embodiments, the inner tubular member further includes a ramp on the outer surface of the inner tubular member. In some embodiments, the outer tubular member is slidably movable over the ramp to elevate at least a portion of the outer tubular member above the inner tubular member. In some embodiments, the cutting member on the outer tubular member is elevated when the outer tubular member is in the extended position. In some embodiments, the soft tissue cutting device further includes one or more balloons coupled to the outer tubular member that expand radially inward from the outer tubular member.

A second aspect of the disclosure provides a soft tissue cutting device including: an inner tubular member including a ramp on an outer surface of the inner tubular member, and an internal chamber extending between an inner tube distal and an inner tube proximal end; an outer tubular member including a cutting member on a proximal end of the outer tubular member, wherein the outer tubular member is disposed around a portion of the inner tubular member, and is movable from an initial position to an extended position; a thumb slide attached to an outer surface of the outer tubular member; a locking mechanism removably attached on a proximal end to a distal end of the inner tubular member; and a syringe removably attached to a distal end of the locking mechanism. In some embodiments, the soft tissue cutting device further includes a thumb slide housing disposed around a portion of the inner tube distal end, wherein the thumb slide extends through a portion of a surface of the thumb slide housing.

A third aspect of the invention provides a method of using the soft tissue cutting device of the first or second aspect by: inserting a proximal end of the cutting device in a subject's body region; applying pressure to the dispensing member to release a medicinal agent into the subject's body region; moving the outer tubular member toward the proximal end of the cutting device, thereby causing the cutting member to elevate; cutting a soft tissue in the subject's body region; and moving the outer tubular member toward the distal end of the cutting device. In some embodiments, the medicinal agent is a local anesthetic. In some embodiments, the subject's body region is a subject's hand. In some embodiments, the soft tissue is a transverse carpal ligament or an annular ligament of the finger. In some embodiments, the annular ligament of the finger is an A1 pulley.

These and other embodiments are described in greater detail in the detailed description which follows. An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE DRAWINGS

FIGS. 4A-4C illustrate a side view of a soft tissue cutting device performing a trigger release procedure.

DETAILED DESCRIPTION

The presently disclosed subject matter, which will now be described more fully, can be embodied in different forms and should not be construed as limited to the embodiments set forth herein. The following detailed description is exemplary in nature and is not intended to limit the scope, applicability, or configuration of the disclosure in any way. Rather, the following description provides some practical illustrations for implementing examples of the present disclosure. Examples of constructions, materials, dimensions, and manufacturing processes are provided for selected elements, and all other elements employ that which is known to those of ordinary skill in the field of the disclosure. Those skilled in the art will recognize that many of the noted examples have a variety of suitable alternatives.

The cutting device disclosed herein is suitable for cutting soft tissue, and can be used to cut any desired soft tissue in the body. In certain embodiments, the soft tissue cutting device is a transverse carpal ligament cutting device that cuts a transverse carpal ligament in a carpal tunnel region. As described above, a CTR procedure involves cutting a transverse carpal ligament in order to reduce median nerve compression and carpal tunnel pressures in the carpal tunnel region. In some embodiments, the soft tissue cutting device is a pulley cutting device. In some examples, the pulley is an A1 pulley of a finger, and the soft tissue cutting device is a trigger release device that cuts the A1 pulley. While each finger has several pulleys, the A1 pulley is the pulley that is most often involved in a condition called trigger finger. The A1 pulley is an annular ligament of the finger that sits near the head of the metacarpal bone, and lies in the flexor groove in the deep transverse metacarpal ligament. The A1 pulley, together with other annular pulleys, and cruciate pulleys, governs the flexor mechanism of the hand and wrist. The A1 pulley provides biomechanical support to the underlying metacarpophalangeal joint, and maintains joint stability and flexor tendon alignment. In a patient with trigger finger, the A1 pulley becomes inflamed or thickened, making it harder for the flexor tendon to glide through it as the finger bends. Over time, the flexor tendon may also become inflamed and develop a small nodule on its surface. When the finger flexes and the nodule passes through the pulley, there is a sensation of catching or locking. This condition, known as trigger finger or stenosing tenosynovitis, can be accompanied by pain or stiffness. The trigger release procedure involves cutting or releasing the A1 pulley to enable the flexor tendon to glide freely.

While the illustrated embodiments show an exemplary embodiment of a soft tissue cutting device, as noted above, it should be understood that the presently disclosed subject matter can be embodied in different forms and should not be construed as limited to the embodiments set forth herein below. Furthermore, the soft tissue cutting device of the current device may be used for other types of soft tissue cutting procedures.

Throughout the specification, in the embodiments generally shown herein, "distal" as used herein, shall generally refer to being closest to the target tissue when the soft tissue cutting device is inserted into the target tissue, and "proximal" as used herein, shall generally refer to being furthest from the target tissue when the soft tissue cutting device is inserted into the target tissue.

Figure 1:
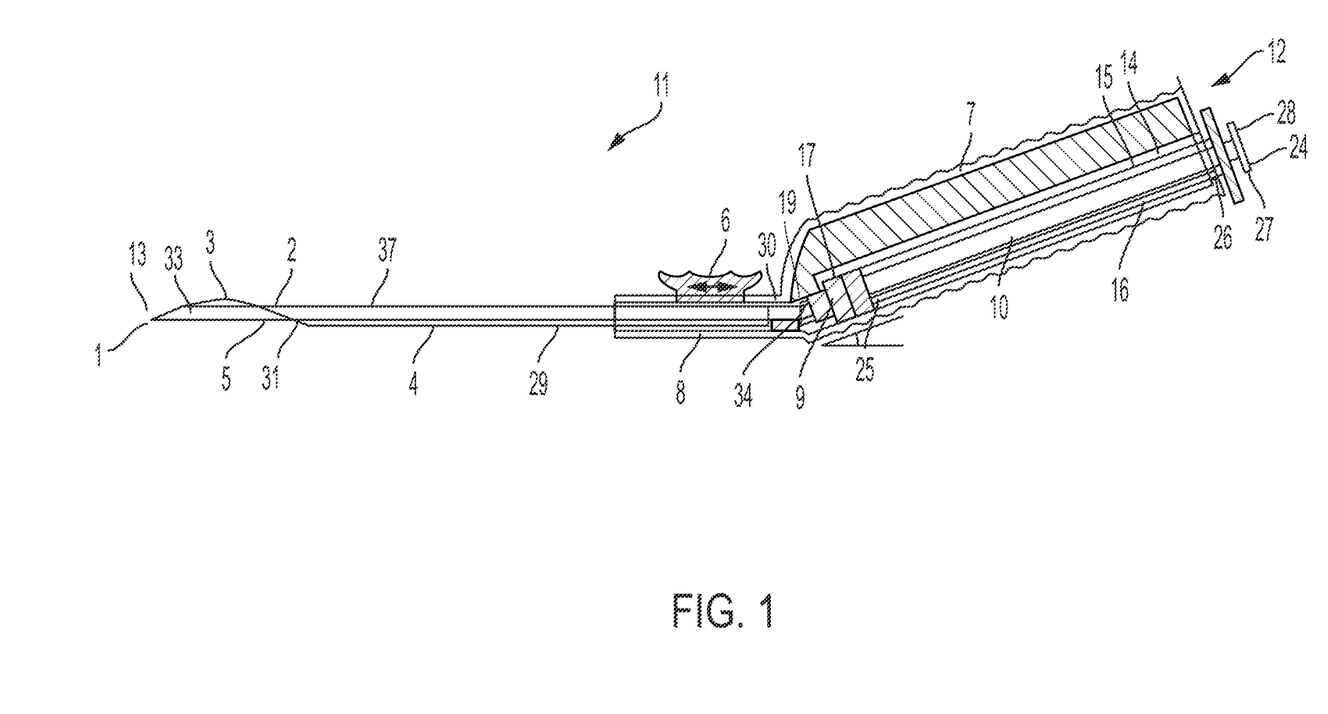
FIG. 1 illustrates a side view of a soft tissue cutting device.

FIG. 1 is a side view of an embodiment of a soft tissue cutting device 11. The soft tissue cutting device 11 may include a distal end 13 and a proximal end 12. The proximal end 12 may be configured to enable an operator to control various functions on the distal end 13 of the soft tissue cutting device 11. The distal end 13 may be configured to perform various functions, including cutting soft tissue in a body, and dispensing a medicinal agent, such as for example a numbing, pain relieving, or pain prevention agent, such as, for example, a local anesthetic. The proximal end 12 of the soft tissue cutting device may include a handpiece 7.

In some embodiments, the handpiece is configured to allow an operator to operate the device using a single hand only. In some embodiments, the single-hand handpiece is a handle that includes one or more controls on the handle (e.g., top, bottom, sides, etc.) such that the operator can use a finger to operate one or more controls. However, skilled artisans will understand that the single-hand handpiece is merely one embodiment of the present invention and is not required. Alternately, two hands or even two operators can operate the present device.

In some embodiments, the handpiece is molded. The handpiece can be molded in a configuration that provides a comfortable hold for the user when performing at least one of the cutting device injection or cutting functions. For example, finger grip indentations, raised ridges, etc. may be provided on the handpiece.

As shown in FIG. 1, within the handpiece 7 is a recess 14 that runs along the length of the handpiece 7, and that can receive the barrel 15 of a dispensing member 16. Thus, when a dispensing member 16 is inserted in the recess 14, the handpiece 7 is disposed at least partially around the dispensing member 16. In some embodiments, the dispensing member 16 is a syringe. At the distal end 17 of the recess 14, a removable attachment mechanism 9 may be disposed for removably coupling the dispensing member 16 (e.g., the barrel of the dispensing member 16) to the proximal end 19 of the inner tubular body 5. In some embodiments, the attachment mechanism 9 is a locking mechanism, such as for example, a luer lock. Optionally, other attachment mechanisms such as a threaded slot for receiving and end of the dispensing member, a fitted slot, or the like are within the scope of this disclosure. In some embodiments, the dispensing member is a syringe, and the attachment mechanism is a luer lock. Optionally, the dispensing member may be an external plunger in fluid communication with the recess 14.

As shown in FIG. 1, the barrel 15 of the dispensing member 16 forms a compartment for receiving a fluid (e.g., a medicinal agent, a therapeutic agent, a contrast fluid, or the like) and at least a portion of a depressible member 10. The depressible member 10 may be movable from an initial position to an extended position within the barrel 15. In the initial extended position, the depressible member 10 is positioned at least partially toward a proximal end 28 of the barrel 15. The initial position provides a space for the medicinal agent to reside in the barrel 15. In the extended position, the depressible member 10 is positioned toward a proximal end 28 of the dispensing tube 22. In the fully depressed position, the depressible member 10 is positioned at the distal end 25 of the barrel 15. As the depressible member 10 is moved from the initial to or toward the depressed position, at least a portion of any fluid within the dispensing member 16 is forced into the inner tubular body 5 of the soft tissue cutting device 11.

The dispensing member may, optionally, include or may be in communication with an actuator or controller that controls functions of the dispensing member. In some embodiments, the control may be positioned on the dispensing member. As shown in FIG. 1, in some cases, the controller 27 is located on the proximal end 28 of the depressible member 10. In some cases, the depressible member 10 is a plunger, and the controller 27 is a plunger flange located on the proximal end of the plunger. In some embodiments, the depressible member is a syringe, and the controller is a plunger flange located on the proximal end of the syringe plunger.

In some embodiments, the controller may be positioned outside of the handle. For example, the control can be a lever, slider button, push button and/or clamp. In some embodiments, the controller is a slider button positioned on an external surface of the handpiece. The slider button can be coupled to a plunger to control movement of the plunger. In some embodiments, the slider button is directly connected to the plunger. In some embodiments, the controller is a clamp. In such cases, the clamp can be coupled to a plunger to control movement of the plunger. Optionally, the controller may be a motor that controls the movement of the plunger.

As shown in FIG. 1, the handpiece 7 may be coupled to an outer tubular body 4 soft tissue cutting device 11. The outer tubular body 4 may form a hollow channel 29 running along the length of the outer tubular body 4, from the proximal end 30 to the distal end 31, such that an inner surface of the outer tubular body 4 defines the hollow channel 29.

The handpiece can be coupled to the outer tubular body using a variety of different configurations. In some cases, the handpiece and outer tubular body have a permanent junction. For example, the handpiece and outer tubular body can have a set angular junction or a set straight junction. In other cases, the handpiece and outer tubular body have an adjustable junction that can be adjusted to accommodate operator preference. In other cases, the handpiece and outer tubular body have a rotatable junction that can be rotated to accommodate operator preference. For example, the handpiece and outer tubular body can have a junction that is adjustable in length or angulation or rotation. In yet other cases, the handpiece and the outer tubular body can have a removable junction so that the handpiece and the outer tubular body are removable from one another.

As noted above, the handpiece can be arranged at any suitable angle from the outer tubular body. In some embodiments, the angle between the handpiece and the outer tubular body is adjustable. Examples of such angles can include, without limitation, between 175 degrees and 140 degrees, between 170 degrees and 150 degrees, or between 165 degrees and 155 degrees. In some embodiments, the angle between the handpiece and the outer tubular body is about 160 degrees.

The outer tubular body can also be provided as a single piece or as a plurality of different pieces. In some cases, the outer tubular body extends from the distal end to the proximal end as a single piece. In other cases, the outer tubular body extends from the distal end to the proximal end as a plurality of pieces. The outer tubular body is formed of any desired medically acceptable material.

As shown in FIG. 1, residing within at least a portion of the hollow channel 29 of the outer tubular body 4 may be an inner tubular body 5. Thus, the inner tubular body 5 has a diameter that is smaller than the diameter of the outer tubular body 4. Within the inner tubular body 5 lies a hollow internal chamber 33 extending through the length of the inner tubular body, from the proximal end 34 to the distal end 1, such that an inner surface of the inner tubular body 5 defines the internal chamber 33. The inner tubular body 5 may be configured to deliver a fluid (e.g., a medical agent, a contrast agent, etc.), withdrawn from the dispensing member 16, to a subject's body. In some embodiments, the inner tubular body 5 may be a syringe needle. The inner tubular body may be formed of any desired medically acceptable material.

As noted above, and shown in FIGS. 1-3B, the outer tubular body 4 is disposed around at least a portion of the inner tubular body 5. The distal end 31 of the outer tubular body 4 may include a cutting member 2 that is sufficiently sharp to cut through soft tissue. In some embodiments, the cutting member 2 is a blade having a cutting edge 36. The cutting edge 36 may be created using any now or hereafter known methods such as, without limitation, etching, grounding, or the like.

In some embodiments, the cutting member 2 is located on an upper region 37 (or outside) of the distal end 31 of the outer tubular body 4. The outer 4 and inner 5 tubular bodies are configured so that when the cutting member 2 is not in use, the inner surface of the outer tubular body 4 resides in close proximity to the outer surface of the inner tubular body 5, such that the cutting member 2 resides in close proximity to the outer surface of the inner tubular body 5 and is not exposed. By "close proximity" is meant that the inner surface of the outer tubular body 4 is sufficiently close to the outer surface of the inner tubular body 5, that when the soft tissue cutting device 11 is inserted into a body tissue, in the inactive position, the cutting member 2 will not cut the tissue, while at the same time, the inner surface of the outer tubular body 4 is sufficiently far from the outer surface of the inner tubular body 5, that the outer tubular body 4 can move freely over the inner tubular body 5. Thus, the proximity of the inner 5 and outer 4 tubular members in the inactive position serves to protect against premature cutting of the tissue, without hindering the movement of the outer tubular body 4. In some embodiments of the invention, in the inactive position, the inner surface of the outer tubular body is about 0.5 mm-3.5 mm, 0.5 mm-1 mm, 1 mm-1.5 mm, 1.5 mm to about 2 mm, about 1 mm to about 2.5 mm, 2.5 mm-3.5 mm, etc., from the outer surface of the inner tubular body.

The outer tubular body and the inner tubular body can have any desired cross-section shape, as long as the shape does not interfere with the functioning of the device. In some embodiments, at least one of the outer or inner tubular bodies has a circle-shaped tubular cross-section shape. In some embodiments, at least one of the outer or inner tubular body has a non-circle-shaped tubular cross section shape. For example, in some cases, at last one of the outer or inner tubular body has a square-shaped tubular cross section shape, rectangle-shaped tubular cross section shape or square-shaped tubular cross section shape with round edges. In some embodiments, the outer and inner tubular bodies have the same cross-section shape. In some embodiments, the outer and inner tubular bodies have a different cross-section shape The outer tubular body and the inner tubular body have any desired size that does not interfere with the functioning of the device, and that is suitable for the medical procedure being performed. As the outer tubular body extends from the distal end to the proximal end, it can maintain the same diameter, or it can assume a different diameter. In some cases, as the outer tubular body extends from the distal end to the proximal end, it increases in diameter. In other cases, as the outer tubular body extends from the distal end to the proximal end, it increases in diameter. Optionally, the outer tubular body may either be coaxial with the inner tubular body and/or the central axis of inner tubular body may be offset from the outer tubular body.

The outer tubular body is movable from an initial position to an extended position. In the initial position, the soft tissue cutting device is in the inactive position, and the outer tubular body is in close proximity with the inner tubular body, as described above, and the cutting member is not exposed to cut tissue that the soft tissue cutting device comes into contact. In the extended position, the outer tubular body moves from its initial position to a position closer to the distal end of the soft tissue cutting device, and elevated away from the outer surface of the inner tubular body. In this elevated position, when the soft tissue cutting device is exposed to soft tissue it is oriented so that it will cut the tissue. The elevation of the cutting member can be achieved in any suitable manner, as described below.

Figure 2A:
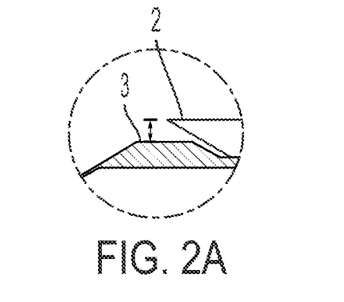
FIG. 2A illustrates an enlarged side view of a cutting member of a soft tissue cutting device, where the cutting device is elevated on a ramp.
Figure 2B:
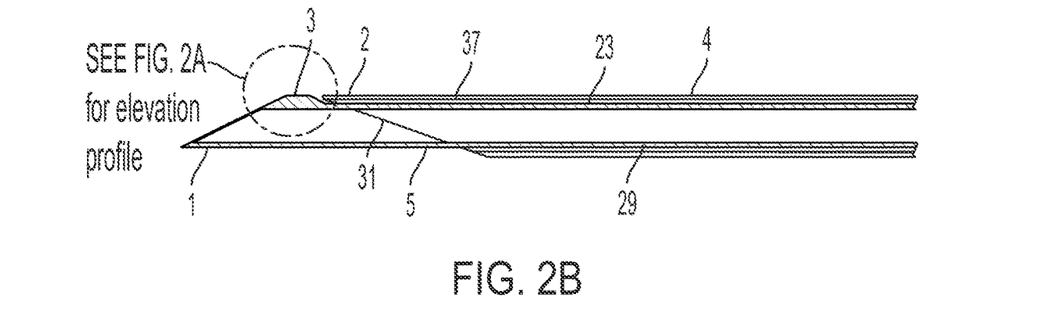
FIG. 2B illustrates a side view of a proximal region of a soft tissue cutting device in an inactive position.
Figure 2C:
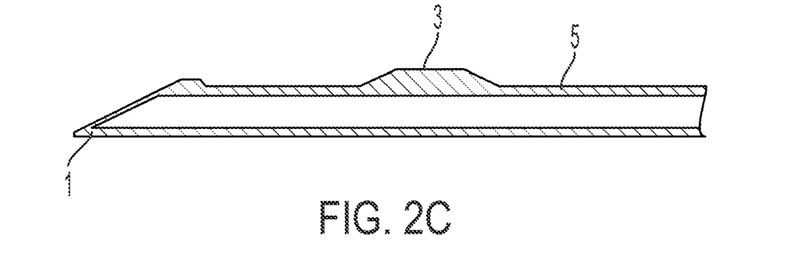
FIG. 2C illustrates an inner tubular body having a ramp located distal to the proximal end of the inner tubular body.
Figure 3A:
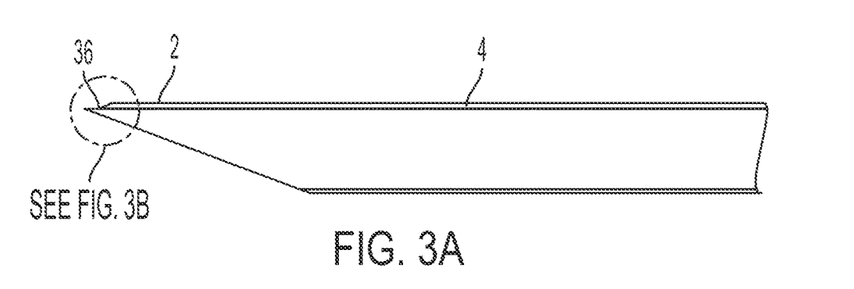
FIG. 3A illustrates a side view of the proximal end of an outer tubular body having a blade with a cutting edge.
Figure 3B:
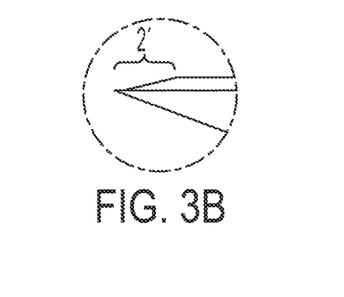
FIG. 3B illustrates a side view of a blade with a cutting edge located at the proximal end of an outer tubular body.

As shown in FIGS. 1-2C, in some embodiments, the elevation of the cutting member 2 is achieved by a ramp 3 located on the outer surface of the inner tubular body 5. The cutting member 2 may be slidably movable over the ramp 3 to elevate the cutting member. The ramp 3 is located on the inner tubular body 5 such that when the outer tubular body 4 is moved from the initial position toward the extended position, the cutting member 2 on the outer tubular body 4 makes contact with the ramp 3, and the ramp 3 causes the cutting member 2 to elevate at least partially over the ramp 3, thereby exposing the cutting member 2 and positioning it for cutting the soft tissue. Thus, the ramp 3 and the cutting member 2 are located on the same, upper plane of the inner 5 and outer 4 tubular bodies, respectively. It will be understood by those of ordinary skill in the art that the ramp and cutting member can be located on any suitable plane on the inner and outer tubular body, respectively, as long as the ramp is positioned so as to cause the cutting member to elevate. In some embodiments, the ramp and the cutting member are located on the upper portion of the inner and outer tubular body, respectively.

The ramp can be located at any suitable location along the length of the inner tubular body. In some embodiments, the ramp 3 is located toward the distal end 1 of the inner tubular body 5 (FIGS. 1 and 2B). In some embodiments, the ramp 3 is located between the distal end 1 and the midpoint (not shown) of the length of the inner tubular body 5 (FIG. 2C). In some embodiments, the ramp is located between the distal end and the proximal end of the length of the inner tubular body. In some embodiments, the ramp is located at the midpoint of the length of the inner tubular body.

In some embodiments, the soft tissue cutting device also has one or more balloons coupled to the outer tubular body that expand radially inward from the outer tubular body. In some cases, the outer tubular body is movable by inflating and deflating a blade balloon elevator. When inflated, the blade balloon elevator elevates the cutting member above the inner tubular body, and when deflated, it lowers the cutting member back to close proximity with the inner tubular body.

As noted above, the outer tubular body is movable from an initial position to an extended position. The outer tubular body may be caused to move by any suitable means. In some embodiments, the outer tubular body can be moved by an outer tubular body movement mechanism. As show in FIG. 1, in some embodiments, the movement mechanism may be a thumb slide 6 attached to the outer tubular body 4. The thumb slide 6 can be pushed in the proximate or proximal direction, and when so pushed, it causes the outer tubular body 4 to move in concert with it. In some embodiments, the movement mechanism may also include a thumb slide housing 8 that is disposed around a portion of the distal end 30 of the outer tubular body 4. A portion of the thumb slide housing 8 may define a linear cutout (not shown) in the thumb slide housing 8. The portion of the thumb slide 6 that is attached to the outer tubular body 4 extends through the linear cutout (not shown). The linear cutout (not shown) prevents the thumb slide 6 from causing the outer tubular body 4 to rotate. In some embodiments, the thumb slide is lockable. By "lockable" is meant that the thumb slide may be caused to remain in one position, preventing it from moving. Any suitable means can be used to cause the thumb slide to lock the outer tubular body in position, such as for example, using a spring latch.

This disclosure also provides a method of using the soft tissue cutting device. As noted above, the cutting device is capable of cutting any soft tissue. A medicinal agent, such as for example a local anesthetic is drawn into the dispensing tube, for example, by inserting the distal end of a sterilized cutting device into a container of the agent, and moving the depressible member from the depressed position to the initial extended position. In some embodiments, the amount of medicinal agent drawn into the dispensing tube may be determined based on the intended use. The distal end of the soft tissue cutting device is then placed into a region of the subject's body, and advanced to the vicinity of the cutting location. The medicinal agent is injected into, and optionally around the soft tissue to be cut, by relocating the distal end of the cutting device to different locations and depressing the depressible member, thereby releasing at least a portion of the medicinal agent from the inner tubular body. The distal end of the cutting device is then positioned at the desired cutting site. After placement in a suitable position for cutting the soft tissue, the outer tubular body is caused to move toward the distal end of the cutting device to expose the cutting member. In some embodiments this movement of the outer tubular body is performed by using a finger or thumb to push forward a thumb slide connected to the outer tubular body. The outer tubular body is advanced in the distal direction of the cutting device, until the cutting member is caused to elevate. In some embodiments, this elevation is caused by the distal end of the outer tubular body rising at least partially over a ramp on the inner tubular body. As the outer tubular body is elevated, the cutting member at the distal end of the outer tubular body is exposed, and cuts the target tissue. As the cutting device is advanced through the soft tissue, it continues to cut the tissue. When the desired portion of the soft tissue has been cut, the outer tubular body is caused to move back toward the proximal end of the cutting device. In some embodiments this movement of the outer tubular body is performed by using a finger or thumb to pull back a thumb slide connected to the outer tubular body. The soft tissue cutting device is then safely removed from the subject's body.

The method can be performed with the aid of an ultrasound device that enables the user of the soft tissue cutting device to visualize the tissues below the epidermis and safely perform the procedure.

Figures 4A, 4B, 4C:
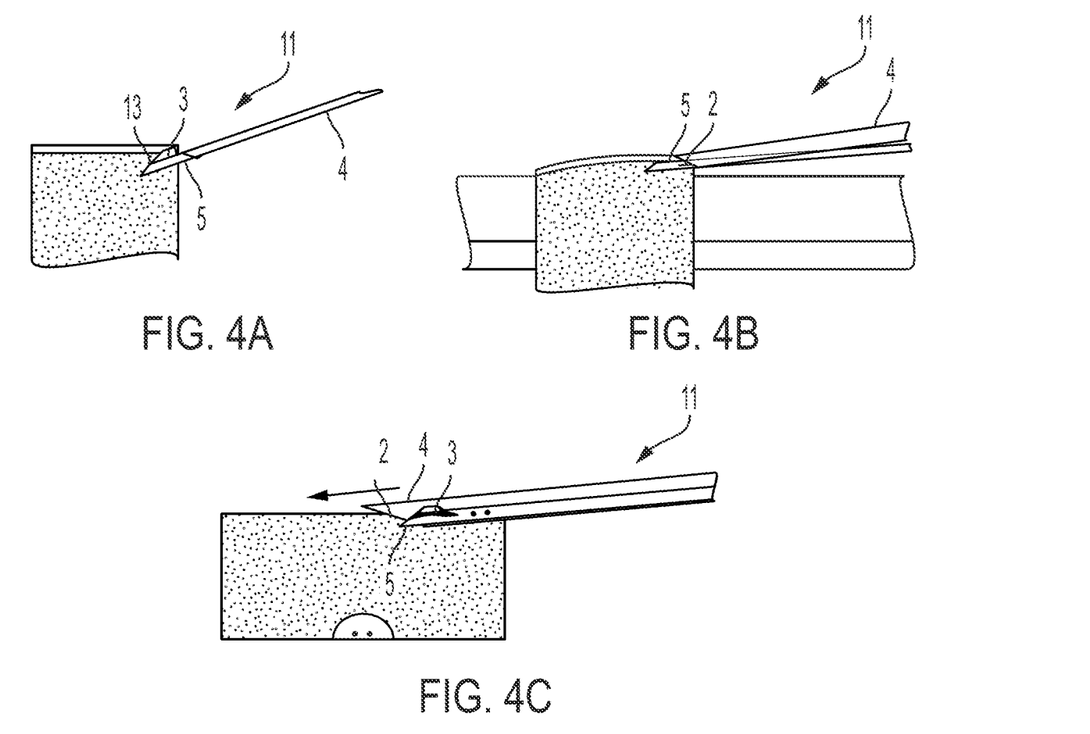
FIG. 4A illustrates the soft tissue cutting device in an inactive position inserted deep to an A1 pulley for injection of a suitable fluid between the A1 pulley and the surrounding tissue (e.g., flexor tendon)
FIG. 4B illustrates the soft tissue cutting device with the outer tubular body elevated on a ramp.
FIG. 4C illustrates the soft tissue cutting device in an active position with the cutting member cutting the A1 pulley.

In some embodiments, the method is used to cut a transverse carpal ligament transverse carpal ligament. In some embodiments, the method is used to cut an annular ligament, such as for example, a pulley, such as for example, an A1 pulley in a subject's hand. As noted above, the A1 pulley overlies the metacarpophalangeal joint, and maintains joint stability and flexor tendon alignment. During a trigger release procedure, the A1 pulley is cut or released to enable the flexor tendon to glide freely. FIGS. 4A-4C shows a side view of an A1 pulley being cut using the soft tissue cutting device 11, according to the method. FIG. 4A shows the soft tissue cutting device 11 in an inactive position, with its distal end 13 inserted deep to the A1 pulley, where it injects a medicinal agent. FIG. 4B shows the soft tissue cutting device 11 with the outer tubular body 4 in the process of being elevated on a ramp (not shown), preparing to cut the soft tissue. FIG. 4C shows the soft tissue cutting device 11 in an active position with the outer tubular body 4 fully extended, and the cutting member 2 cutting the A1 pulley.

Figure 5A:
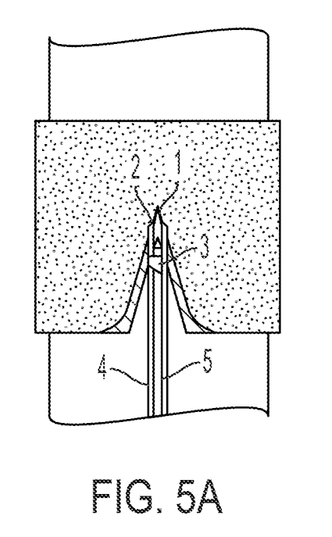
FIG. 5A illustrates a top view of a soft tissue cutting device in active position, having a ramp at the proximal end of the inner tubular body, where the soft tissue cutting device is cutting through an A1 pulley.
Figure 5B:
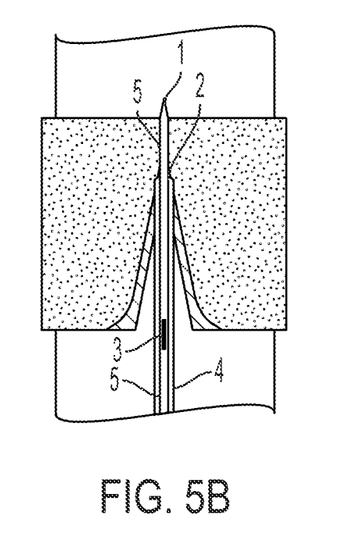
FIG. 5B illustrates a top view of a soft tissue cutting device in active position, having a ramp located distal to the proximal end of the inner tubular body, where the soft tissue cutting device is cutting through an A1 pulley.

FIGS. 5A and 5B show a top view of an A1 pulley being cut using the soft tissue cutting device 11, according to the method. FIG. 5A shows an A1 pulley being cut by a soft tissue cutting device 11 having a ramp 3 located toward the distal end 1 of the inner tubular body 5. FIG. 5A shows an A1 pulley being cut by a soft tissue cutting device 11 having a ramp 3 located distally on the inner tubular body 5.

While the above disclosure describes an embodiment of a soft tissue cutting device including a outer tube with a cutting member disposed around an inner tube configured to dispense fluid in a subject tissue, the disclosure is not so limiting.

Figure 6A:
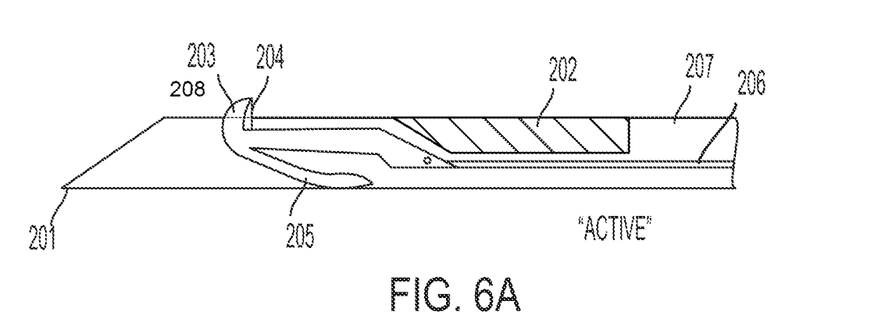
FIG. 6A illustrates a side view of a hollow tube and cutting member of an alternate embodiment of a soft tissue cutting device in an active position.
Figure 6B:
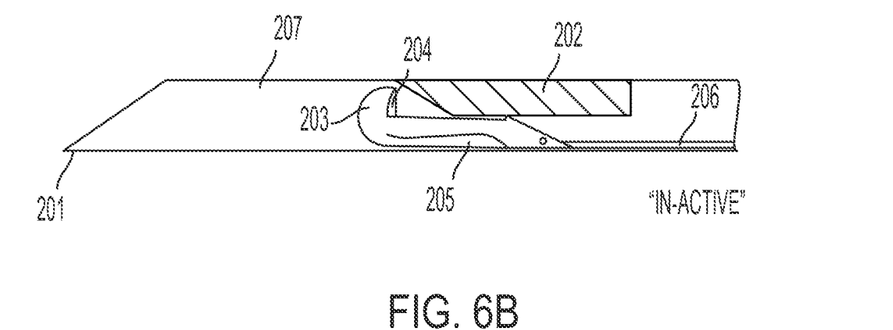
FIG. 6B illustrates the cutting member of FIG. 6A in an inactive position.

For example, FIGS. 6A and 6B illustrate an alternative embodiment of single tube including a cutting member that can be used to replace the outer and inner tube combination in the soft tissue cutting device described above. As shown in FIG. 6A, the arrangement may include a single hollow tube 207 that has a crimp (or another structure like an upside down ramp) 202 in the anterior aspect of the hollow tube 207. A hook shaped (or any other suitable shape) cutting member 203 may be biased such that in an inactive position (shown in FIG. 6B), the cutting member is at least partially stored between the crimp 202 and the inner wall of the hollow tube 207, and a cutting edge 204 of the cutting member 203 is completely sheathed inside the hollow tube 207. For example, a biasing member 205 (such as a spring) may be provided which when compressed allows the cutting member 203 to be stored between the crimp 202 and the inner wall of the hollow tube 207 in the inactive position. However, when the cutting member 203 is pushed out of from stored between the crimp 202 and the inner wall of the hollow tube 207, the biasing member 205 may be decompressed allowing the cutting edge 204 to be exposed through a slot 208 (provided on the same side that includes the crimp) in the superior aspect of the hollow tube 207 (as shown in FIG. 6A). Optionally, the cutting member 203 is pushed out of from stored between the crimp 202 and the inner wall of the hollow tube 207 the cutting member 203 by pushing a handle 206 from the proximal end towards the distal end (for example, using a thumb slide mechanism as discussed above).

It should be noted that while FIGS. 6A and 6B only illustrate the hollow tube and the cutting member with the biasing arrangement, the hollow tube 207 may be coupled to the handle and/or the dispensing member of the soft tissue cutting device shown in FIGS. 1-3B such that the hollow tube 207 may receive a suitable fluid from a dispensing member and may inject it from the distal tip 201 before, after, and/or while the cutting member is in an active position (as described above).

Figure 7:
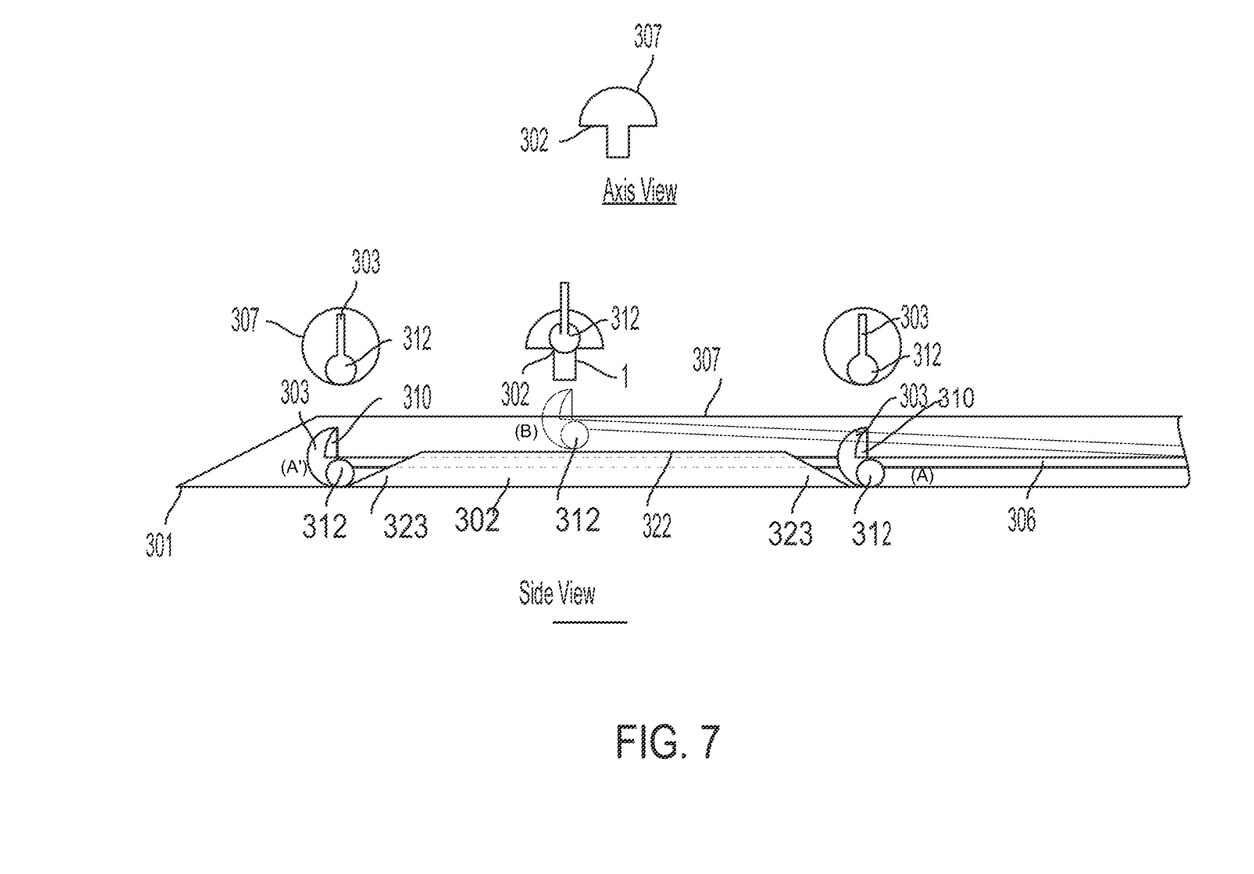
FIG. 7 illustrates a side view of yet another embodiment of a soft tissue cutting device.

FIG. 7 illustrates yet another configuration that includes a cutting member 303 within a single hollow tube 307 including a slot 304. The hollow tube has a crimp (e.g., a ramp) 302 in the inferior aspect of the hollow tube 307. The crimp 302 may be configured to include a ramp including an incline 321, a flat plane 322, and a decline 323. A hook shaped (or any other suitable shape) cutting member 303 may be provided such that in an inactive position A or A', the cutting member is completely sheathed inside the hollow tube 307. However, when the cutting member 303 moves over the incline 321 to rest over the flat plan 322 (position B), and the cutting edge 310 to be exposed through a slot 308 in the superior aspect of the hollow tube 307. Optionally, the cutting member 303 may be pushed over the crimp 302 the cutting member 303 by pushing or pulling a handle 306 from the proximal end towards the distal end (or vice versa) using, for example, a thumb slide mechanism as discussed above. The cutting member may include a cutting member guide 312 for stabilizing the cutting member 303 as it moves up and down the crimp 302.

It should be noted that while FIG. 7 only illustrate the hollow tube and the cutting member that can move over the crimp, the hollow tube 307 may be coupled to the handle and/or the dispensing member of the soft tissue cutting device shown in FIGS. 1-3B such that the hollow tube 307 may receive a suitable fluid from a dispensing member and may inject it from the distal tip 301 before, after, and/or while the cutting member is in an active position (as described above).

While different embodiments of a soft tissue cutting device are described, skilled artisans will understand that any of the features of one embodiment can be incorporated into the other embodiments. Any combination of the features described in any of the embodiments can be included in the soft tissue cutting device and are within the scope of the invention. It should be noted that while the current disclosure describes use of the soft tissue cutting device for carpal tunnel surgery, the disclosure is not so limiting and the soft tissue cutting device can be used during, for example, surgery of extensor compartment of the wrist, surgery of retinacula tissue of the ankle, surgery of cubital tunnel of the elbow, or the like.

In some embodiments, the soft tissue cutting device of this disclosure may also be used during hydrodissection procedures to, for example, inject fluid around the anatomical structure (e.g., a compressed nerve). Such fluid may be a contrast agent that creates a visible working space between planes of tissue for enhanced ultrasound visibility, may be fluid that frees a compressed nerve from scar tissue or lesions that trap it, or the like.

Similarly, the soft tissue cutting device of this disclosure may also be used during electorsurgery (e.g., devices that perform cutting using bipolar electrodes) for, for example, injecting electrically conductive fluids such as saline in and/or around the target tissue.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of cutting a transverse carpal ligament in a patient, the method comprising:
   inserting a distal end of an inner tubular member of a cutting device into a wrist of the patient and under the transverse carpal ligament, wherein an outer surface of the inner tubular member comprises a ramp;
   advancing an outer tubular member over the inner tubular member to cause the outer tubular member to ride over the ramp to cut the transverse carpal ligament; and
   removing the cutting device from the wrist.

2. The method of claim 1, further comprising:
   attaching a distal end of a syringe barrel to an attachment mechanism on a handle of the cutting device; and
   advancing a fluid from the syringe barrel through the inner tubular member and into the wrist.

3. The method of claim 2, wherein the fluid comprises a medicinal agent.

4. The method of claim 3, wherein the medicinal agent is a local anesthetic.

5. The method of claim 2, wherein the attachment mechanism comprises a luer lock.

6. The method of claim 1, further comprising retracting the outer tubular member over the inner tubular member before removing the cutting device from the wrist.

7. The method of claim 1, wherein the ramp is located near the distal end of the inner tubular member.

8. The method of claim 1, wherein advancing the outer tubular member over the inner tubular member comprises advancing a thumb slider coupled with a handle of the cutting device and the outer tubular member.

9. The method of claim 8, further comprising moving the thumb slider to at least one of an advanced position or a retracted position to lock the thumb slider and prevent the outer tubular member from moving.

10. The method of claim 1, further comprising inflating a balloon on an outer surface of the inner tubular member before advancing the outer tubular member, wherein the outer tubular member advances over the inflated balloon to cut the transverse carpal ligament.

11. A method of cutting an A1 pulley in an annular ligament of a finger of a patient, the method comprising:
    inserting a distal end of an inner tubular member of a cutting device into the finger of the patient, wherein an outer surface of the inner tubular member comprises a ramp;
    advancing an outer tubular member over the inner tubular member to cause the outer tubular member to ride over the ramp to cut the A1 pulley, wherein a distal end of the outer tubular member comprises a cutting edge; and
    removing the cutting device from the finger.

12. The method of claim 11, further comprising:
    attaching a distal end of a syringe barrel to an attachment mechanism on a handle of the cutting device; and
    advancing a fluid from the syringe barrel through the inner tubular member and into the finger.

13. The method of claim 12, wherein the fluid comprises a medicinal agent.

14. The method of claim 13, wherein the medicinal agent is a local anesthetic.

15. The method of claim 12, wherein the attachment mechanism comprises a luer lock.

16. The method of claim 11, further comprising retracting the outer tubular member over the inner tubular member before removing the cutting device from the finger.

17. The method of claim 11, wherein the ramp is located near the distal end of the inner tubular member.

18. The method of claim 11, wherein advancing the outer tubular member over the inner tubular member comprises advancing a thumb slider coupled with a handle of the cutting device and the outer tubular member.

19. The method of claim 18, further comprising moving the thumb slider to at least one of an advanced position or a retracted position to lock the thumb slider and prevent the outer tubular member from moving.

20. The method of claim 11, further comprising inflating a balloon on an outer surface of the inner tubular member before advancing the outer tubular member, wherein the outer tubular member advances over the inflated balloon to cut the A1 pulley.

21. A method of cutting a transverse carpal ligament in a patient, the method comprising:
   inserting a distal end of an inner tubular member of a cutting device into a wrist of the patient and under the transverse carpal ligament;
   inflating a balloon on an outer surface of the inner tubular member before advancing the outer tubular member;
   advancing an outer tubular member over the inner tubular member and over the inflated balloon to cut the transverse carpal ligament; and
   removing the cutting device from the wrist.

22. A method of cutting an A1 pulley in an annular ligament of a finger of a patient, the method comprising:
   inserting a distal end of an inner tubular member of a cutting device into the finger of the patient;
   inflating a balloon on an outer surface of the inner tubular member before advancing the outer tubular member;
   advancing an outer tubular member over the inner tubular member and over the inflated balloon to cut the A1 pulley, wherein a distal end of the outer tubular member comprises a cutting edge; and
   removing the cutting device from the finger.

* * * * *